United States Patent [19]

Spencer et al.

[11] Patent Number: 4,630,600
[45] Date of Patent: Dec. 23, 1986

[54] ANKLE BRACE AND PROTECTOR

[75] Inventors: Treesa Spencer; Terry Alberta, both of Santa Ana, Calif.

[73] Assignee: Pro-Tec Sports, Inc., Santa Ana, Calif.

[21] Appl. No.: 830,325

[22] Filed: Feb. 18, 1986

[51] Int. Cl.[4] .............................................. A61F 3/00
[52] U.S. Cl. .................................. 128/80 R; 128/89 R
[58] Field of Search ............... 128/80 R, 89 R, 80 A, 128/87 A; 5/481

[56] References Cited

U.S. PATENT DOCUMENTS

| 3,506,000 | 4/1970 | Baker | 128/80 R |
| 4,433,682 | 2/1984 | Badra | 128/80 R |
| 4,476,858 | 10/1984 | Curtis | 128/80 R |
| 4,573,456 | 3/1986 | Spann | 128/80 R |

Primary Examiner—Gregory E. McNeill
Attorney, Agent, or Firm—Edward A. Sokolski

[57] ABSTRACT

An ankle brace and protector has a pair of similar opposing side portions which fit against the ankle and adjacent side portions of the users foot. These side portions are joined together along their rear edges and along the forward portion of their bottom edges by elastic strap members. A front protective pad is attached at its bottom end to one of the side portions. The front and side pad portions have impact resistant material therein. Cinching straps are provided along the front edges of the side pads for use in securing the device to the user's foot with the front pad covering the instep and adjacent portions of the foot and the side portions tightly secured against the ankle and adjacent portions of the user's foot.

7 Claims, 6 Drawing Figures

ANKLE BRACE AND PROTECTOR

This invention relates to protective ankle braces and more particularly such a device which can be secured to a user's ankle and adjacent foot portions to both brace and provide protection against impact.

Many ankle braces are available for bracing a user's ankle and adjacent foot portions, particularly for use after there has been an injury. These devices are usually designed to provide bracing and do not provide adequate protection against impact. Particularly in sports such as football, soccer, ice hockey and the like where there is not only a danger of injury due to straining movements of the wearer but also due to impact, many injuries are sustained due to inadequate protection for the athlete.

The device of the present invention provides protection for the user's ankle and adjacent foot portions and prevents injuries not only due to stressing movements of the wearer but also due to impact so as to lessen the hazard of injury to these foot portions.

Briefly described, the device of the present invention has a pair of opposing side pad portions which are lined with a high impact resisting material such as a suitable high density urethane plastic foam. A front pad also having a high impact padding therein is attached to one of the side pads at one corner thereof. Elastic strap members interconnect the rear edges and a portion of the bottom edges of the side pad members. Cinching straps are provided along the front edges of the side pads for use in tightly securing the brace to the user's foot with the user's heel extending through an opening between the bottom and rear elastic straps and with the bottom elastic strap abutting against the bottom of the user's foot and the rear elastic strap abutting against the rear of the user's foot. In this manner, the ankle and adjacent portions of the foot are both braced and protected against impact by the side pads with the instep being protected by the front pad.

It is therefore an object of this invention to provide an improved ankle brace and protector.

It is a further object of this invention to provide a device useful for protecting a user's foot by bracing the ankle and adjacent portions and by providing protection against impact.

Other objects of this invention will become apparent as the description proceeds in connection with the accompanying drawings of which:

Figure 1:
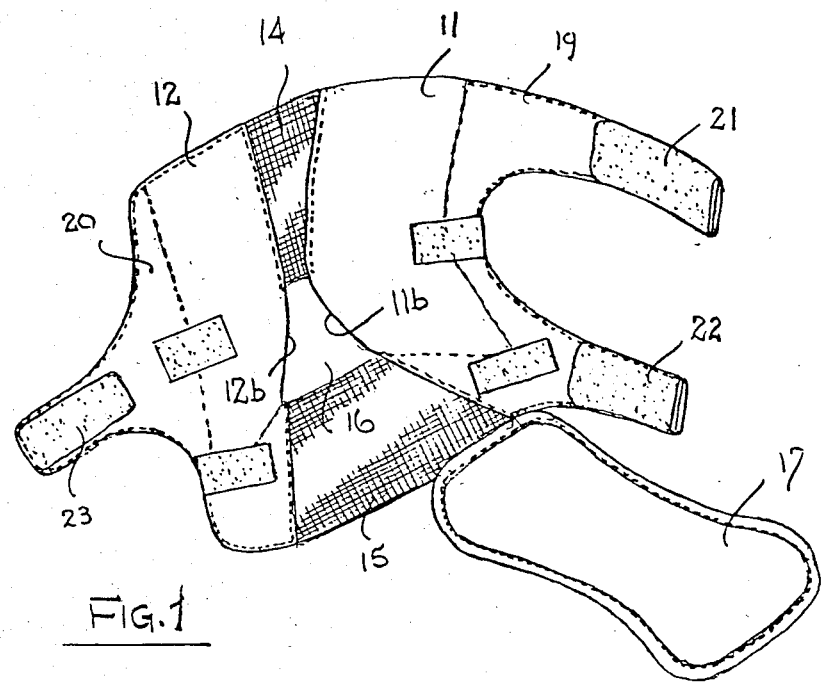
FIG. 1 is a perspective view of a preferred embodiment of the invention.
Figure 2:
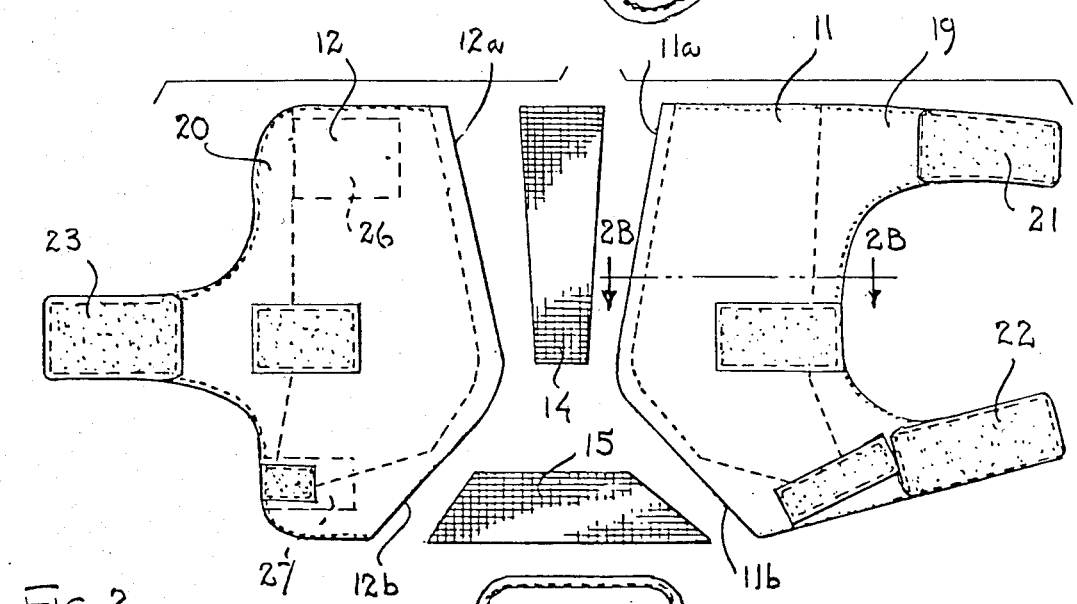
FIG. 2 is an exploded view of the preferred embodiment.
Figure 2A:
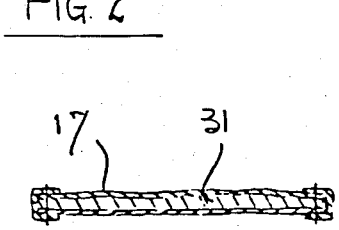
FIG. 2a is a cross sectional view taken on the plane indicated by 2a—2a in FIG. 1.
Figure 2B:
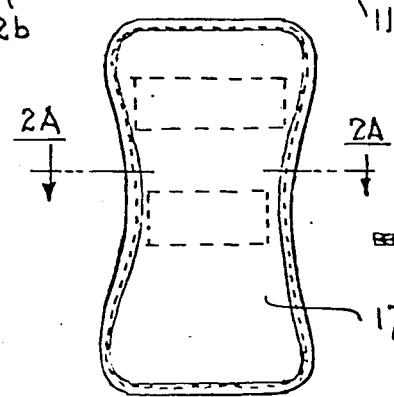
FIG. 2b is a cross sectional view taken on the plane indicated by 2b—2b in FIG. 1.
Figure 3:
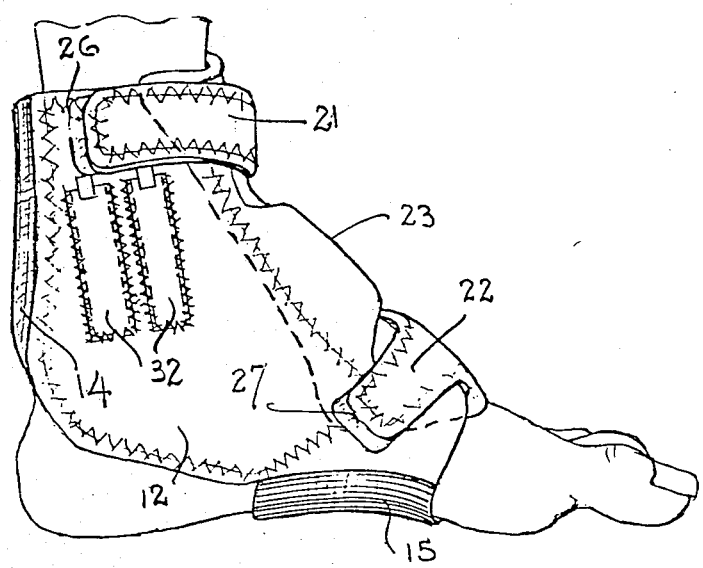
FIG. 3 is a side elevational view illustrating the preferred embodiment installed on the foot of a user.
Figure 4:
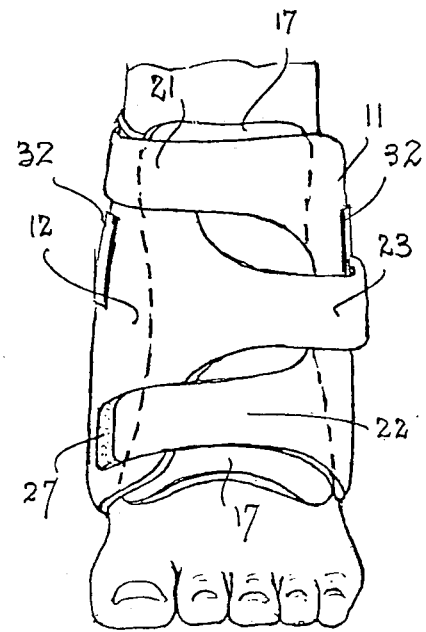
FIG. 4 is a front elevational view showing the device of the invention installed on the foot of a user.
Figure 5:
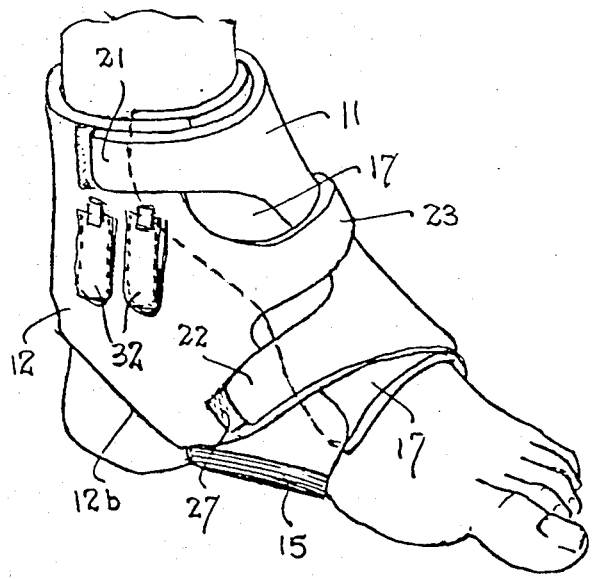
FIG. 5 is a perspective view illustrating the preferred embodiment installed on the foot of a user.
Figure 6:
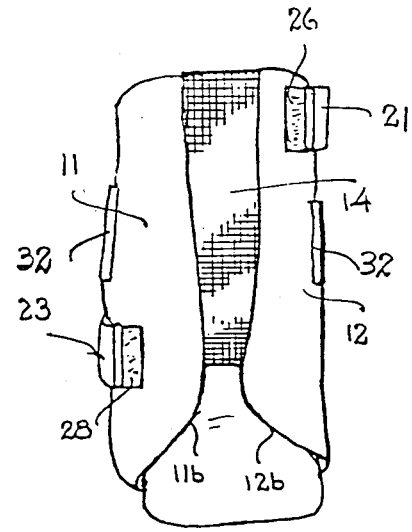
FIG. 6 is a rear elevational view showing the preferred embodiment installed on the foot of a user.

Referring to FIGS. 1, 2, 2a and 2b, a preferred embodiment of the device of the invention as illustrated. The device includes a pair of side pads 11 and 12 which are joined together along their rear edges 11a and 12a by an elastic strap member 14. The front portions of the bottom edges 11b and 12b are joined together by elastic strap 15 leaving an open space 16 between the rear portions of such bottom edges. A front pad member 17 is stitched along one of its edges to the bottom of pad member 11. Side pads 11 and 12 have respective flap portions 19 and 20 extending therefrom. Side flap portion 19 has a pair of cinch straps 21 and 22 while said flap 20 has a single such cinch strap 23. The cinch straps 21-23 have Velcro material thereon and operate in connection with Velcro pads 26-28 to tightly cinch the brace to the user's ankle and adjacent foot portions as best can be seen in FIGS. 3-6. Pads 11, 12 and 17 have an impact resisting padding material 30 and 31 as best can be seen in FIGS. 2a and 2b which material can be stitched into the pads. Such material may comprise polyurethane foam or other similar padding material.

Referring now to FIGS. 3-6, the device of the invention is shown installed for use. As can be seen, the device is cinched tightly around the user's foot by means of Velcro straps 21-23 and their corresponding Velcro fasteners 26-28 to bring side pads 11 and 12 into tight abutment against the user's ankle and with front pad 17 in tight abutment against the user's instep with the user's toes protruding through the front of the device and the user's heel protruding out from the rear of the device. Elastic strap 14 runs along the rear of the user's foot while elastic pad 15 runs along the bottom of the foot. Thus, it can be seen that bracing is provided for the user's ankle portions by side pads 11 and 12, these side pads and front pad 17 also providing protection against blows which the foot might receive. A pair of pockets 32 for retaining weights are provided should it be desired to provide additional ankle strengthening exercise.

While the invention has been described and illustrated in detail, it is to be clearly understood that this is intended by way of illustration and example only and is not to be taken by way of limitation. The spirit and scope of this invention being limited only by the terms of the following claims.

We claim:

1. A device for protecting and bracing the ankle and adjacent portions of a user's foot comprising a pair of similar opposing side pads adapted to fit against said ankle portion, said side pads having rear and bottom edges, first elastic strap means for joining together the rear edges of said side pads, second elastic strap means for joining together the front portions of the bottom edges of said side pads, there being a space between the first and second elastic strap means for receiving the user's heel, flap portions extending laterally from each of said side pads, each of said flap portions having cinch strap means extending therefrom for cinching the side pads against the user's ankle, and front pad member means attached to one of said side pads for covering and protecting the user's instep.

2. The device of claim 1 wherein said side pads are lined with impact resisting material.

3. The device of claim 1 wherein the front pad means is attached at one corner thereof to a bottom corner of one of said side pads.

4. The device of claim 1 wherein said cinch strap means each includes a Velcro fastener.

5. The device of claim 2 wherein the front pad is lined with impact resisting material.

6. The device of claim 4 wherein the cinch strap means of one of said flap portions includes a first cinch strap attached to one of said side pads and wrapped around the user's foot above the ankle and a second cinch strap attached to said one side pad and wrapped around the user's instep, the other of said cinch strap means comprising a single cinch strap attached to the other of the side pads and wrapped around the user's instep.

7. The device of claim 1 and additionally including pocket means formed on one of said side pads and weight means retained in said pocket means.

* * * * *